United States Patent [19]
Galician

[11] 4,134,401
[45] Jan. 16, 1979

[54] EYE-PATCHING METHOD AND DEVICE

[76] Inventor: Kenneth M. Galician, 4321 NW. 110 Ave., Coral Springs, Fla. 33065

[21] Appl. No.: 799,950

[22] Filed: May 24, 1977

[51] Int. Cl.$^2$ ............................................. A61F 13/12
[52] U.S. Cl. ..................................................... 128/163
[58] Field of Search .............. 128/157, 163, 260, 268, 128/76.5, 334 R, 335; 2/15

[56] References Cited

U.S. PATENT DOCUMENTS

| | | | |
|---|---|---|---|
| 2,572,638 | 10/1951 | Loos | 128/163 |
| 2,798,492 | 7/1957 | Barnes et al. | 128/335 |
| 2,818,865 | 1/1958 | Jacoby | 128/334 R |
| 3,068,863 | 12/1962 | Bowman | 128/163 X |
| 3,402,716 | 9/1968 | Baxter | 128/335 |

*Primary Examiner*—Lawrence W. Trapp

[57] ABSTRACT

In a preferred embodiment, in medical care of a person's eye, for varying indications such as post operative patching, treatment of corneal injury, non-surgical tarsorrhaphy, exposure keratitis, situations where patient removing and reapplying of the patch independently is desired, and in occlusion therapy in amblyopia, peeking through the patch being impossible, the method of use of one or more of several combinations are desirable, there being a narrow adhesive strip of length to bind-over a major part of the closed upper and lower lids, and an elongated absorbent material impregnated preferably with medicament, for aligning along and over the eye-slit of the closed upper and lower eyelids, and a gauze sponge, and a tape element having a predetermined size in area sufficient to substantially cover upper and lower eyelids in a closed state and having a bottom adhesive surface adapted to fasten the tape element to skin surfaces of the upper and lower eyelids when in a closed state, for the placing thereof over one or more of the adhesively attached adhesive strip at least with or without other noted elements.

9 Claims, 9 Drawing Figures

EYE-PATCHING METHOD AND DEVICE

This invention relates to a novel method and device for improved eye-patching in the medical treatment of the eye.

BACKGROUND TO THE INVENTION

Prior to the present invention, patching of a persons eye has been plagued with a variety of problems and difficulties. First of all, many persons for reasons of vanity, have arbitrarily refused to accept an unsightly eye-patch even though the use and need of such is direly indicated and advised by the doctor. Secondly, for the patient who will not strenuously resist the use of an eye patch, reasonable skill and experience are normally required for neatly, effectively and securely applying an eye-patch. It is not unusual for an applied eye-patch to be so loose that the eyelids move beneath the patch, with accompanying discomfort as well as possible further irritation of the already sick eye. An open eye in close contact with patch material may moveover cause damage to the eye surfaces themselves, thereby doing more harm than good if not properly applied. Even when properly applied, an eye-patch can be large and cumbersome, and clearly uncomfortable, together with being aesthetically unappealing even for those persons willing to submit to the temporary wearing of the eye-patch. Very important, also, is the fact that rarely is it possible for a patient to effectively and correctly apply his own patch, or to remove and reapply a prior applied patch, for reasons already stated above.

In addition, from the standpoint of the experienced practitioner who is schooled and qualified in proper eye-patching and eye care, time required heretofore to properly administer and apply the eye-patch has added to the burdon of the doctor already heavily pressed for time because of overload of patients in need of treatment, versus insufficient hours available for the patient load.

SUMMARY OF THE INVENTION

Accordingly, objects of the present invention include the overcoming and avoiding of problems of the types and difficulties discussed above, together with novel advantages.

Another object is to obtain an eye-patching device adaptable to a variety of optional uses interchangeably, as might otherwise require substantially different conventional treatments for the differing indications, evolving from different eye disorders or different ophthalmic treatments.

Another object is to obtain a novel method employing such a device, together with advantages of simplicity of application and lack of need of expert qualifications, speed of application being at an optimal rate, cost of components and nursing or attendant being minimal, applicability to many diverse indications and conditions and situations being optimal, and ability of a patient to self-apply, or to remove and reapply being readily possible together with great safety and effective application.

Another object is to obtain such a device and method of use, suitable for indications such as post operative patching, treatment of corneal injury, non-surgical tarsorrhaphy, exposure keratitis, occlusion therapy in amblyopia, and the like.

Other objects become apparent from the preceding and following disclosure.

One or more objects are obtained by the invention illustrated in the accompanying Figures which are for the purpose of making possible improved understanding of the invention, but not necessarily limiting of the scope thereof to those specific illustrations, the invention extending to obvious variations as apparent to a skilled artisan.

Broadly the invention may be described as each of a method and a device for eye-patching, made possible by the device as follows, applied by the method as hereinafter described.

The eye-patching device includes a combination of two or more elements, of which at least one thereof is a narrow strip having an adhesive coating on an underface thereof; other elements include an elongated absorbent material preferably impregnated with medicament, and a gauze sponge, and a tape element. In a more full description, the narrow strip preferably has a further narrowed width at a point about mid-way intermediate between opposite ends relative to a longitudinal axis along the length of the strip, and the narrow strip is of a length sufficient to substantially overlap a major portion of each of upper and lower eyelids, such that by virtue of the adhesive coating which is preferably contact adhesive, closed upper and lower securely held in the closed state. The absorbent material of elongated shape is suitable for aligning with and applying to the eye-slit of the closed upper and lower eyelids, but may — as dependent upon the condition being treated, be treated or impregnated with medicinal media, preferably mounted on the large tape element. The gauze sponge is optional & of a size and shape suitably adapted for placing over the absorbent material before application of the tape element, but may be utilized devoid of the absorbent elongated material described above, as conditions might make possible. The tape element is of a size having an area and shape approximating the lid surfaces of the upper and lower eyelids in a closed state of a patient being treated, and has a bottom adhesive surface (underside surface of adhesive material) suitable for adhering to the outer skin surface of the upper and lower eyelids in a closed state, facilitating the holding closed of the lids while also securely and firmly holding the other elements — if any, in proper place.

THE FIGURES

FIG. 1 illustrates an elevation in-part view of a person's eye, showing the upper and lower eyelids in a closed state fastened utilizing the method of the present invention and an element of the eye patching device.

FIG. 2, the same view as FIG. 1, illustrates additionally the placing of the elongated absorbent material along and over the slit of the closed eyelids, a subsequent step in the method.

FIG. 3, the same view as FIGS. 1 and 2, illustrates additionally a gauze sponge placed over the elongated absorbent material and the narrow strip of FIG. 1, a further subsequent step in the method.

FIG. 4, also the same view as prior Figures, illustrates the large tape element adhered over and onto the prior-noted elements and the upper and lower eyelids. FIG. 4AA merely illustrates appearance of the FIG. 4 patch, mounted on a face.

DETAILED DESCRIPTION OF THE INVENTION

Figure 1:
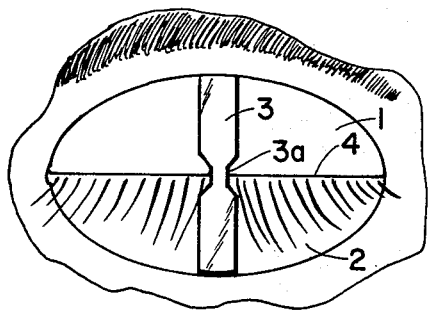
FIG. 1A illustrates a side elevation view of the narrow strip of FIG. 1, showing the plastic strip having a lower adhesive coating.
Figure 1A:

FIGS. 1 and 1A each basically illustrate the narrow strip 3 having a narrowed portion 3a, and typically plastic layer 8 having an adhesive coating 9, preferably contact adhesive, shown in FIG. 1 in an applied state, as would be the first act therewith after bringing-together the upper and lower eyelids.

Figure 2:
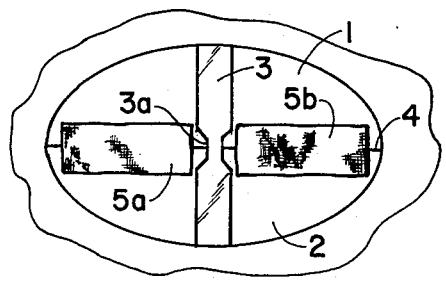
FIG. 2A illustrates a side elevation view of the elongated absorbant material, showing the shallow thickness of the fabric of typically about two-ply, of the FIG. 2 illustration.
Figure 2A:
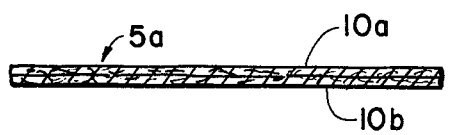

FIGS. 2 and 2A each basically illustrate the elongated absorbent material, two being utilized in FIG. 2 placed along and over the eye-slit 4 as elongated absorbent materials 5a and 5b, only 5a being illustrated in FIG. 2A, showing the two-ply fabric (gauze) 10a and 10b.

Figure 3:
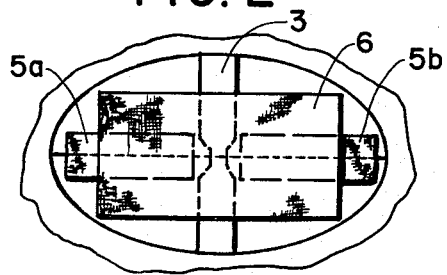
FIG. 3A illustrates a side elevation view of the gauze sponge mounted in FIG. 3, showing the multiply of thick fabric typically of severaly-ply gauze material and enlarged area to cover a major portion of the upper and lower closed eyelids.
Figure 3A:
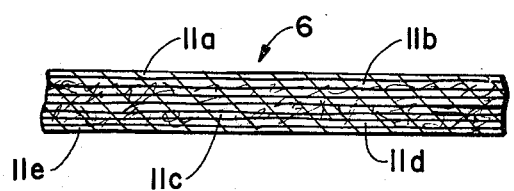

FIGS. 3 and 3A each basically illustrate the gauze sponge which typically includes several thickness (ply) of material, the gauze sponge 6 having typically layers 11a through 11e, and being typically rectangular or oval, as might be desired, a rectangular large surface-area gauze sponge 6 being shown in the FIG. 3, as applied over and against the above-discussed other elements.

Figure 4A:
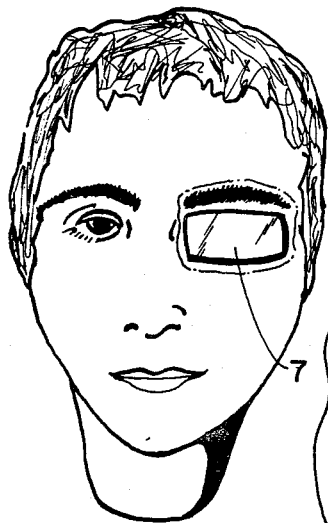
FIG. 4A illustrates a side elevation view of the large tape element which covers a larger area of the upper and lower eyelids, over the other elements as shown in FIG. 4, the FIG. 4A illustrating the plastic layer having an adhesive undercoating.
Figure 4:
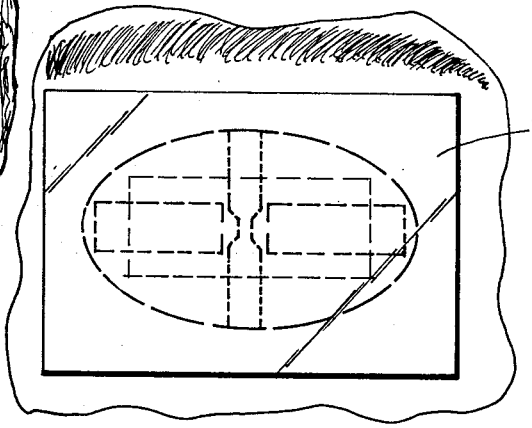
Figure 4A:
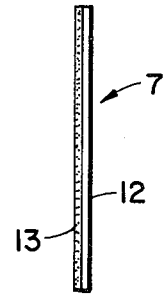

FIGS. 4 and 4A each basically illustrate the large tape element typically of a size to satisfactorily cover and overlap the prior-noted elements to thereby cover also surrounding areas remaining of the upper and lower eyelids, thereby securely holding firmly and securely the one or more prior applied elements.

While the FIGS. 1 through 4 represent the typical order of and position of applying the several noted elements, it is to be understood that not every condition or situation requires the utilization of all. However, it is contemplated that always the narrow strip 3 will be used as a basic tool, and normally the enlarged tape element 7 will also be utilized in combination with the narrow strip 3.

Normally and preferably the elongated strip is provided commercially as purchased. It is also contemplated, however that any other one or more medicament solution &/or solids may impregnate the elongated strip material, such as steroid-antibiotic ointment.

The preferred narrowed or notched portion of the narrow strip reduces the amount of tape and adhesive coating thereof at the edge of the eyelids and accordingly reduces irritation to the lids, adding to comfort if nothing else. The narrowed portion also facilitates the centering of the strip above and below the eye-slit of the closed upper and lower lids.

Typically the dimensions of the several elements are as follow. The narrow strip measures about 3 cm. long, 2 mm. wide at the narrowed point, and 5 mm. wide otherwise (elsewhere). The adhesive, as for all elements, is preferably of the contact type, of any suitable composition conventional to the present trade or as desired. The enlarged tape element 7, is about 2.5 cm. wide and about 5 cm. long, and is preferably transparent. The elongated absorbent material typically is available in pairs, each about 1 cm. wide and about 2 mm. long, but may be a single longer unit. The gauze sponge typically ranges from 5 to 7 cm in length and about 5 cm in height, but may be larger as required to fully cover other elements thereunder, and to adhere to the eyelid surfaces.

Accordingly, above-noted objects are obtained, resulting in speedy administering to patients effectively and efficiently, as well as making possible the utilization of less skilled personnel to perform the patching function, including even permissible self administration by the patient at times, for one or more indications previously noted.

CASE SITUATIONS

In 1976: Multiple instances of successful use at Long Island Jewish Hillside Medical Center, and Queens Hospital Center.

In 1977: Continued success — typical specific examples:

I. Corneal abrasions:

(1) 4/28/77 - Pat.L.F. - OD (right eye) corneal abrasion 2° (secondary) to organic substance; one day with standard (conventional) patch [prior art patch] — abrasion still present; next day patched with Eyeclude (narrow strip of tape vertically, and large tape patch): Patient returned 24 hours later, and the novel patch was still firmly in place, with no slippage, and with patient still unable to open eye (with the patch applied); reported to be comfortable and cosmetically acceptable, pleased; doctor reported the application to be therapeutically successful.

(2) [Second patient] 5/2/77 — Pat.P.B. — OD; time required to apply was 10 sec.; Eyeclude (narrow strip of tape vertically), including as a part thereof large tape patch thereover [in contrast, prior ordinary conventional patches (prior art) typically have been reported by attendant (Queens Hospital Med. Center) to normally require about two minutes to apply properly]. Patient, who did not initially want any patch over his eye, reported the Eyeclude (above-noted) to adhere well, to be comfortable, and that he was willing to wear the same.

II. TREATMENT OF HERPES SIMPLEX:

(1) 4/4/1977: Pat. Ms.S.; OS (left eye). Used only the narrow strip vertically, for patient self-application at about 3 hour intervals at which medication was self-applied to the eye, in treatment of abraded cornea of Herpes Simplex. Patient reported that removal and reapplication was easy and satisfactory. Results was therapeutically successful.

III. TEMPORARY TARSORRCHAPHY

4/77; Pat. L.P.; with decomsated corneal epithelium; vertical narrow strip applied, as a temporizing measure, prior to standard operative tarsorrhaphy procedure. Results satisfactory.

IV. Pat. R.R. After Filtering Surgery

Eyeclude (narrow vertical tape strip, & large tape patch) used in post operative dressing to help obtain firm lid closure. The result reported to be successfully effective therapeutically.

It is within the scope of the invention to make variations and modifications and substitution of equivalents obvious to a person skilled in this particular field, as a part of and extension of the present inventive method and device(s) thereof.

I claim:

1. A method of eye-patching comprising: bringing together the upper and lower eyelids to a closed state; fastening adhesively upper and lower eyelids' outer surfaces together in the closed state by adhesively applying thereto a narrow adhesive-coated strip of predetermined short length of sufficient length to overlap a major portion of each of upper and lower eyelids and of predetermined narrow width sufficient to cover only a minor central portion of an eye-slit such that attachment of upper and lower eyelids is solely centered whereby reduced area of potential irritation and added comfort are obtained, said fastening including placing the narrow adhesive-coated strip at a point within about the central one-third of the length of the eyelids, whereby the eyelids are held in the closed state.

2. A method of claim 1, including applying on top of the narrow adhesive-coated strip and over a major porton of the upper and lower eyelids held in the closed state, a tape element having a size about the same as the two closed eyelids to be covered in area and having a bottom adhesive surface which fastens the tape element to the upper and lower eyelids and the narrow adhesive-coated strip.

3. A method of claim 2, including placing elongated absorbent material along and over the eye-slit of the closed upper and lower eyelids prior to applying the tape element.

4. A method of claim 3, including placing a gauze sponge over said absorbent material prior to said applying of said tape element.

5. An eye-patching device comprising in combination: a narrow adhesive-coated strip of predetermined short length of sufficient length to overlap a major portion of each of upper and lower eyelids and of predetermined narrow width sufficient to cover only a minor central portion of an eye-slit such that attachment of upper and lower eyelids is solely centered whereby reduced area of potential irritation and added comfort are obtained, having an adhesive coating on an underface thereof adapted to be applied adhesively to upper and lower eyelids when in a closed state such that the eyelids are held fastened together in a closed state; and a tape element having a predetermined size in area sufficiently to substantially cover upper and lower eyelids in a closed state and having a bottom adhesive surface adapted to fasten the tape element to skin surfaces of the upper and lower eyelids when in a closed state.

6. An eye-patching device of claim 5, in which said adhesive coating is contact adhesive.

7. An eye-patching device of claim 5, in which said bottom adhesive surface comprises contact adhesive.

8. An eye-patching device of claim 6, including a gauze sponge adapted for placing over the upper and lower eyelids before application of the tape element.

9. An eye-patching device of claim 5, in which the narrow adhesive-coated strip has a further narrowed width at a point about mid-way intermediate between opposite ends relative to a longitudinal axis along the length of the narrow adhesive-coated strip, with length of each of the opposite ends being sufficiently long for and adapted to adhesively anchoring upper and lower eyelids in a closed state when centered along an eye-slit with one-end on an upper eyelid outer surface and with a remaining opposite-end on a lower eyelid outer surface.

* * * * *